US009872664B1

(12) United States Patent
Jin et al.

(10) Patent No.: US 9,872,664 B1
(45) Date of Patent: Jan. 23, 2018

(54) METHODS AND SYSTEMS FOR SCATTER CORRECTION IN POSITRON EMISSION TOMOGRAPHY

(71) Applicant: General Electric Company, Schenectady, NY (US)

(72) Inventors: Xiao Jin, Brookfield, WI (US); Hua Qian, Clifton Park, NY (US); Geng Fu, Rexford, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/390,349

(22) Filed: Dec. 23, 2016

(51) Int. Cl.
*G01T 1/166* (2006.01)
*A61B 6/00* (2006.01)
*A61B 6/03* (2006.01)

(52) U.S. Cl.
CPC .......... *A61B 6/5282* (2013.01); *A61B 6/032* (2013.01); *A61B 6/037* (2013.01); *A61B 6/4417* (2013.01); *A61B 6/50* (2013.01); *A61B 6/5205* (2013.01); *A61B 6/54* (2013.01)

(58) Field of Classification Search
CPC ..................................................... G01T 1/1611
See application file for complete search history.

(56) References Cited

U.S. PATENT DOCUMENTS

| | | | | |
|---|---|---|---|---|
| 6,201,247 B1* | 3/2001 | Lutheran | ............... | G01T 1/1642 250/363.04 |
| 6,490,476 B1* | 12/2002 | Townsend | ............... | A61B 6/032 250/363.03 |
| 9,336,614 B1* | 5/2016 | Wollenweber | ........ | G06T 11/008 |
| 2004/0195512 A1* | 10/2004 | Crosetto | ............... | A61B 6/037 250/363.04 |
| 2006/0004274 A1* | 1/2006 | Hawman | ............... | A61B 6/032 600/407 |
| 2011/0288407 A1* | 11/2011 | Brinks | ................... | A61B 6/032 600/427 |
| 2016/0048615 A1* | 2/2016 | Kolthammer | ......... | G06T 11/005 703/2 |

OTHER PUBLICATIONS

Ren et al., "Abdominal multi-organ sementation of dynamic PET studies using modified fuzzy clustering algorithm," 2015, IEEE Nuclear Science Symposium and Medical Imaging Conference, pp. 1-4.*

(Continued)

*Primary Examiner* — Kiho Kim
(74) *Attorney, Agent, or Firm* — McCoy Russell LLP

(57) ABSTRACT

Methods and systems are provided for medical imaging systems. In one embodiment, a method comprises estimating an external scatter contamination in emission data based on an estimated emission activity originating from anatomies outside a field-of-view (FOV) of a scanner, the anatomies identified based on an image segmentation analysis performed on an image generated in the imaging system, the image generated prior to acquiring the emission data. In this way, a scatter correction applied to the emission data may include both scatter originating within the FOV and outside the FOV, and hence may be more accurate.

16 Claims, 5 Drawing Sheets

(56) References Cited

OTHER PUBLICATIONS

Bidgoli et al., "Correction of oral contrast artifacts in CT-based attenuation correction of PET images using an automated segmentation algorithm," 2007, IEEE Nuclear Science Symposium Conference Record, vol. 5, pp. 3542-3547.*

Ollinger, J., "Model-based scatter correction for fully 3D PET" Physics in Medicine and Biology, vol. 41, No. 1, Jan. 1996, 25 pages.

Watson, C. et al., "A Single Scatter Simulation Technique for Scatter Correction in 3D PET" Three-Dimensional Image Reconstruction in Radiation and Nuclear Medicine, vol. 4, Jun. 30, 1996, 14 pages.

* cited by examiner

METHODS AND SYSTEMS FOR SCATTER CORRECTION IN POSITRON EMISSION TOMOGRAPHY

FIELD

Embodiments of the subject matter disclosed herein relate to non-invasive diagnostic imaging, and more particularly, to image reconstruction using Positron Emission Tomography (PET).

BACKGROUND

PET generates images that represent the distribution of positron-emitting nuclides within the body of a patient. When a positron interacts with an electron by annihilation, the entire mass of a positron-electron pair is converted into two 511-keV photons (also referred to as 511-keV events). The photons are emitted in opposite directions along a line of response (LOR). The annihilation photons are detected by detectors that are placed on both sides of the LOR, in a configuration such as a detector ring. The detectors convert the incident photons into useful electrical signals that can be used for image formation. An image thus generated based on the acquired image data includes the annihilation photon detection information.

A large portion of the emitted photons is scattered (e.g., Compton scattering), before leaving the patient. In order to account for the scattered photons, scatter corrections may be performed using a single scatter simulation (SSS) method. The SSS model estimates scatter occurring within an axial field-of-view (FOV) of the scanner. However, scatter events may originate outside the axial FOV of the scanner. Estimating out-of-field (OOF) scatter may be difficult without knowing the emission activity outside the axial FOV. In certain types of imaging, such as in prospective scanning and reconstruction, the emission activity outside the axial FOV may not be known.

BRIEF DESCRIPTION

In one embodiment, a method comprises estimating an external scatter contamination in emission data based on an estimated emission activity originating from anatomies outside a field-of-view (FOV) of a scanner, the anatomies identified based on an image segmentation analysis performed on an image generated in the imaging system, the image generated prior to acquiring the emission data. In this way, the OOF scatter may be estimated without prior knowledge of the emission activity occurring outside the axial FOV. In one example, the anatomies may be identified using image segmentation analysis performed on an image generated from a computed tomography (CT) scan performed prior to acquiring the emission data via a PET scan. By using CT images acquired prior to the PET scan for estimating OOF scatter, the PET scanning workflow remains unchanged as an auxiliary PET scan to determine the emission activity for OOF scatter estimation is not utilized. As a result, the method may be easily implemented in existing systems.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
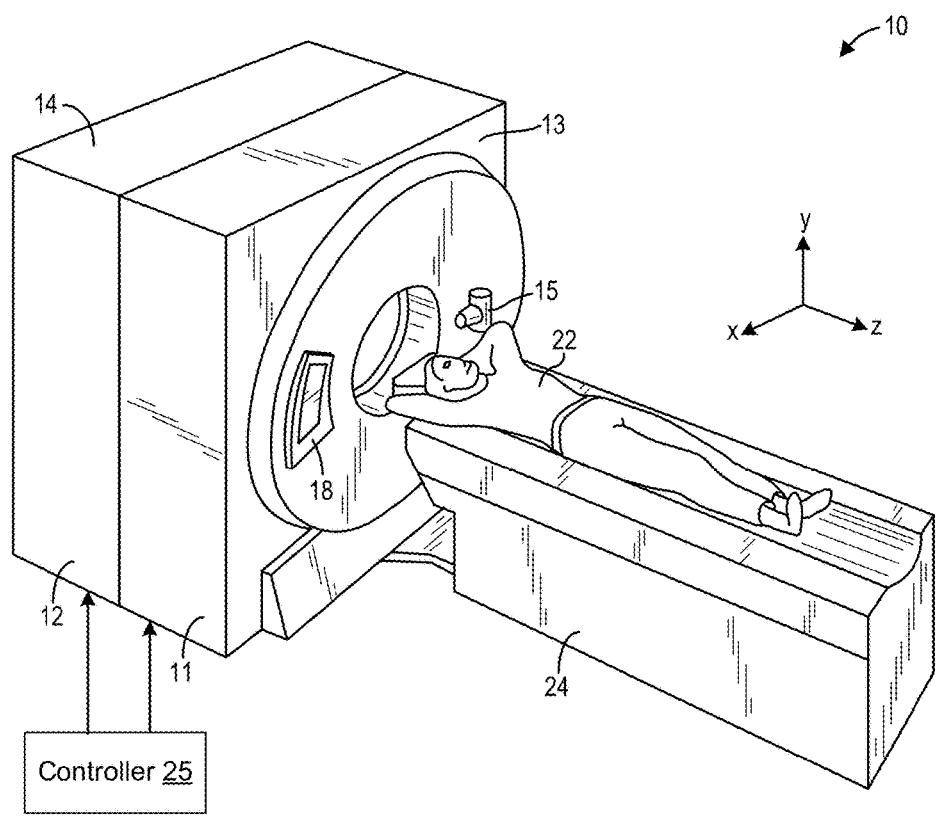
FIG. 1 shows a pictorial view of an exemplary multi-modality imaging system according to an embodiment of the invention.
Figure 2:
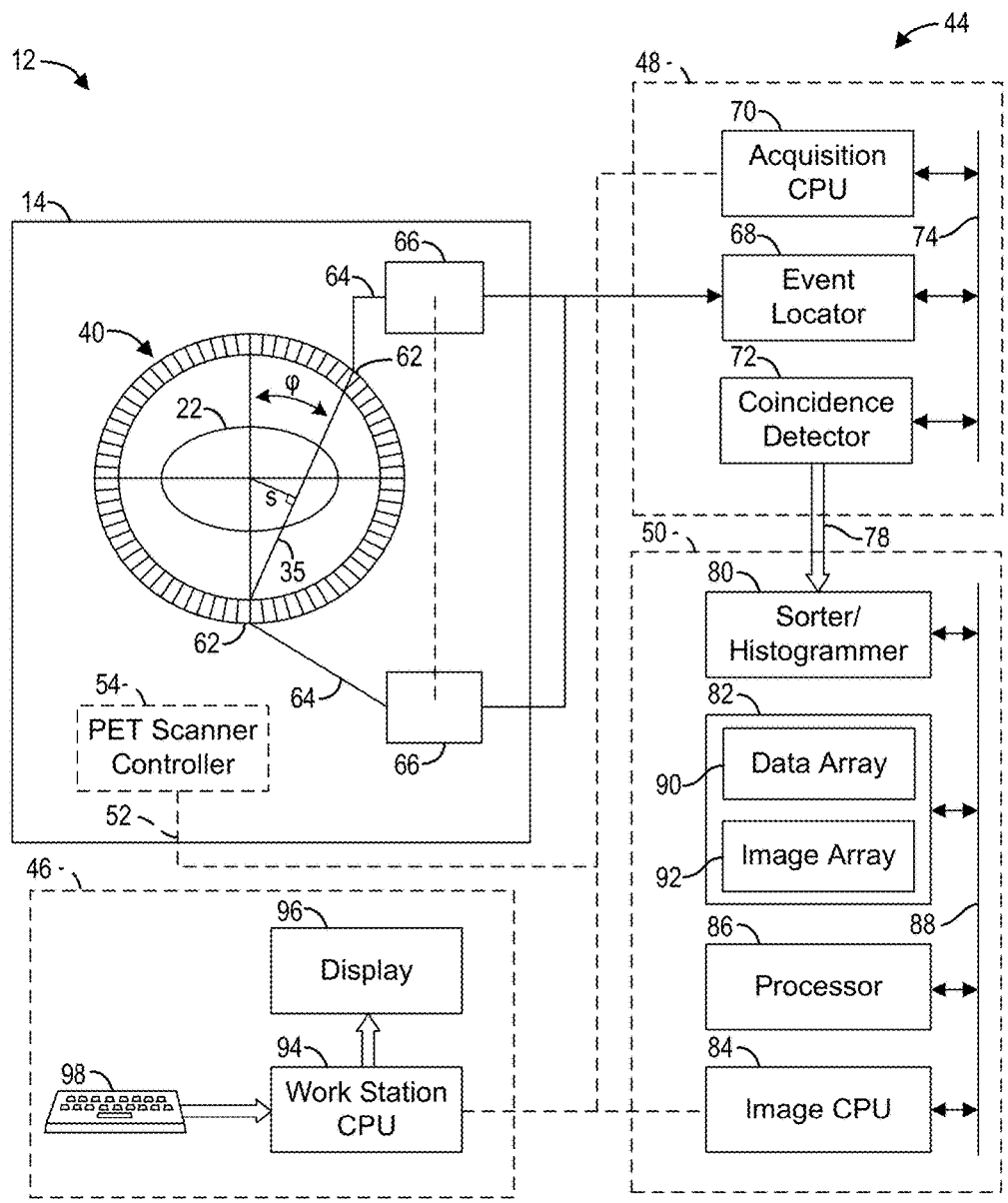
FIG. 2 shows a block schematic diagram of an exemplary positron emission tomography (PET) imaging system according to an embodiment of the invention.

The following description relates to various embodiments of medical imaging systems. In particular, methods and systems are provided for compensating for out-of-field (OOF) scatter events using computed tomography (CT) image segmentation. An example of an imaging system that may be used to acquire images processed in accordance with the present techniques is provided in FIG. 1. Herein, the imaging system may be a multi-modality system. In one embodiment, the multi-modality imaging system may be a Computed Tomography/Positron Emission Tomography (CT/PET) imaging system wherein a first modality is a CT imaging system and a second modality is a PET imaging system (as illustrated in FIGS. 1 and 2, for example).

Figure 3:
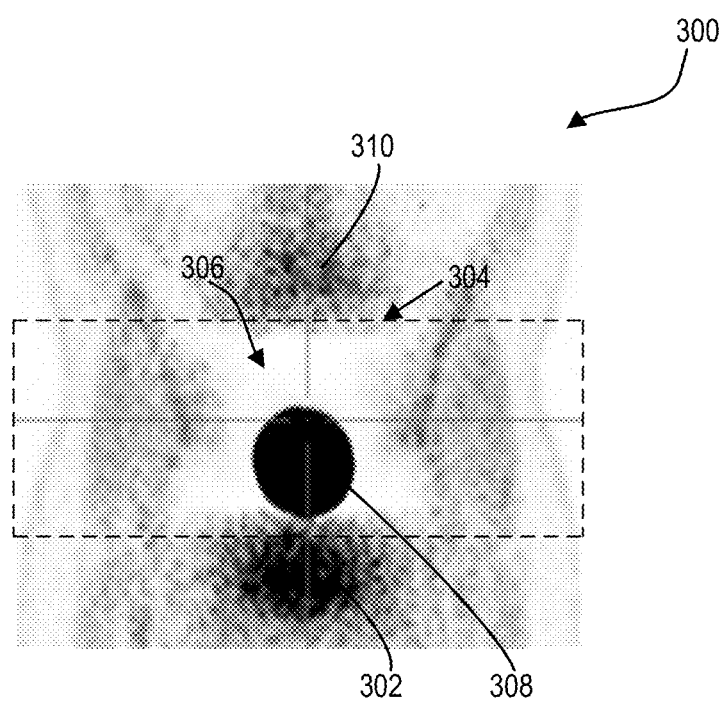
FIG. 3 shows an example PET image with washout artifacts near a bladder having increased emission activity.
Figure 4:
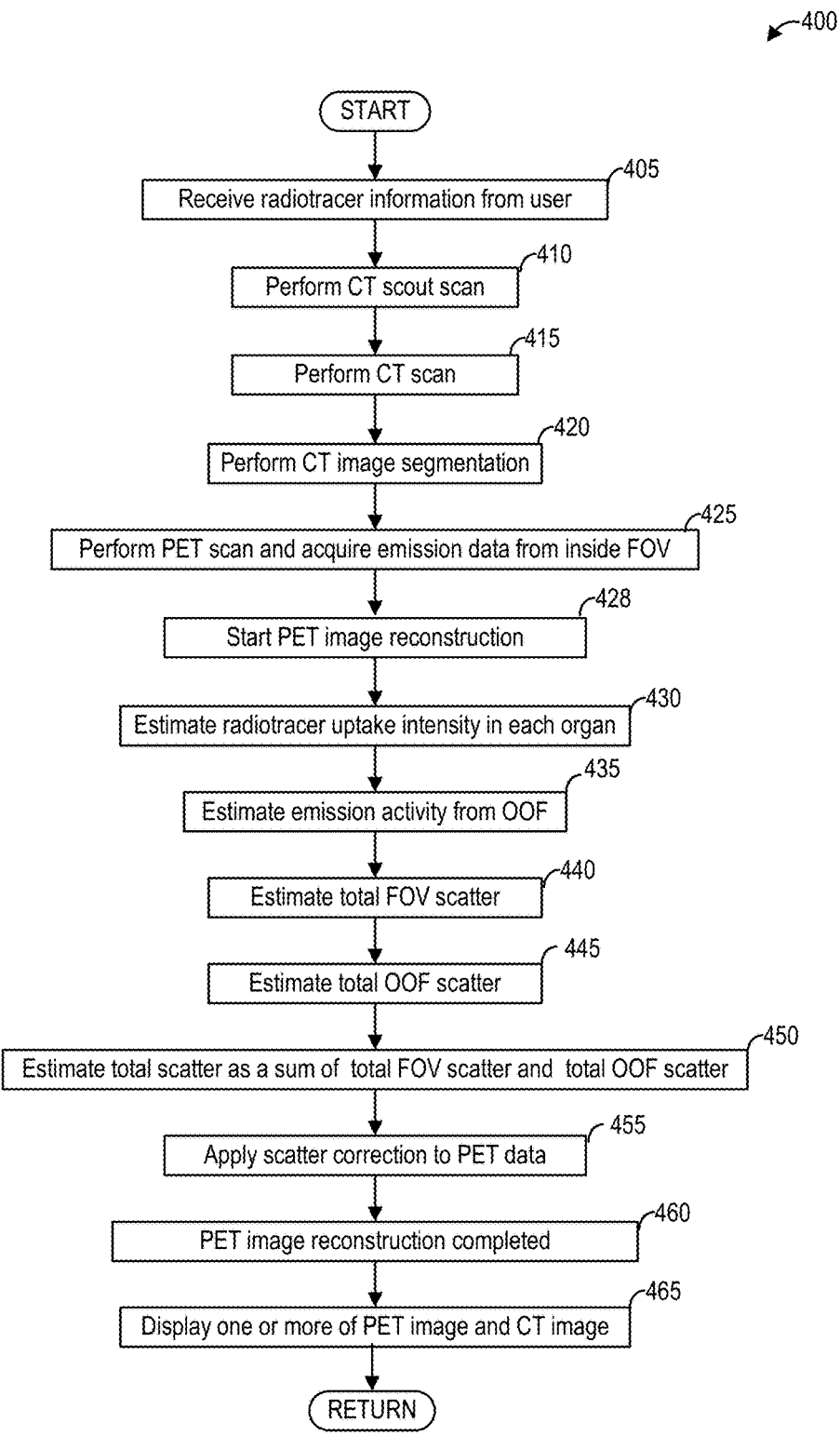
FIG. 4 shows a high-level flow chart illustrating an example method for estimating out-of-field (OOF) scatter in PET imaging system using segmented CT images, according to an embodiment of the invention.
Figure 5:
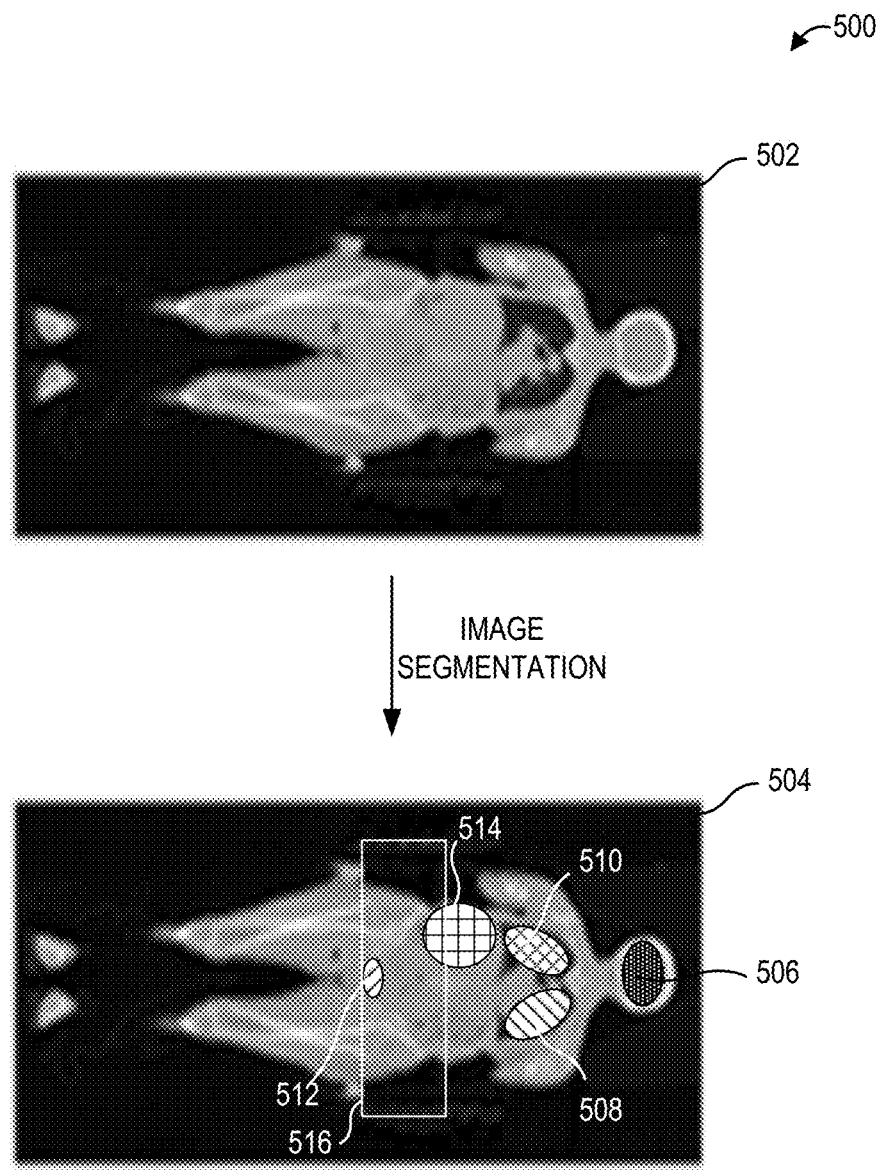
FIG. 5 shows a pictorial view highlighting a process of CT image segmentation, according to an embodiment of the invention.

When an object is scanned using the PET imaging system, scatter events occurring outside an axial field-of-view (FOV) of the scanner may contaminate signals reaching a detector assembly of the imaging system. Such out-of-field (OOF) scatter events may reduce the quality of images generated by the imaging system. For example, image artifacts such as washout artifacts may occur in PET images, as depicted in FIG. 3, when the OOF scatter events are not compensated. A method for estimating the OOF scatter in the PET imaging system by CT image segmentation is shown in FIG. 4. Herein, a CT image is acquired using the CT imaging system prior to acquiring emission data using the PET imaging system and the CT image is further segmented or delineated to identify organs (as shown in FIG. 5) lying outside the FOV of the PET image. The method further includes using the segmented images to estimate emission activity outside the axial FOV. The estimated emission activity from organs lying OOF may then be used to estimate an OOF scatter contribution to the PET emission activity. In this way, a more accurate estimate of scatter events may be achieved. Further, by compensating for the OOF scatter, image quality of the PET images may be enhanced, and image artifacts in the PET images may be reduced. It may be appreciated that the method enables estimating OOF scatter without prior knowledge of emission activity outside the axial FOV. Additionally, the method may not interfere with the current PET scan protocols and therefore may not impact the PET scanning workflow.

Though a CT/PET imaging system is described by way of example, it should be understood that the present techniques may also be useful when applied to images acquired using other imaging modalities, such as CT, tomosynthesis, MRI, ultrasound, and so forth. The present discussion of a CT/PET imaging modality is provided merely as an example of one suitable imaging modality. In other examples, the emission activity of the anatomies lying outside the FOV may be estimated from image data obtained using MRI, ultrasound, or other imaging modalities.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Various embodiments of the invention provide a multi-modality imaging system 10 as shown in FIGS. 1 and 2. Multi-modality imaging system 10 may be a suitable type of imaging system, for example, such as a Positron Emission Tomography (PET), a Single Photon Emission Computed Tomography (SPECT), a Computed Tomography (CT), an ultrasound system, Magnetic Resonance Imaging (MRI), or any other system capable of generating tomographic images. The various embodiments are not limited to multi-modality medical imaging systems, but may be used on a single modality medical imaging system such as a stand-alone PET imaging system or a stand-alone SPECT imaging system, for example. Moreover, the various embodiments are not limited to medical imaging systems for imaging human subjects, but may include veterinary or non-medical systems for imaging non-human objects.

Referring to FIG. 1, the multi-modality imaging system 10 includes a first modality unit 11 and a second modality unit 12. The two modality units enable the multi-modality imaging system 10 to scan an object or patient in a first modality using the first modality unit 11 and in a second modality using the second modality unit 12. The multi-modality imaging system 10 allows for multiple scans in different modalities to facilitate an increased diagnostic capability over single modality systems. In one embodiment, multi-modality imaging system 10 is a Computed Tomography/Positron Emission Tomography (CT/PET) imaging system 10, e.g., the first modality 11 is a CT imaging system 11 and the second modality 12 is a PET imaging system 12. The CT/PET system 10 is shown as including a gantry 13 associated with a CT imaging system and a gantry 14 that is associated with a PET imaging system. For example, the CT imaging system may generate anatomical images of a patient, while the PET system may generate functional images corresponding to dynamic occurrences such as metabolism. As discussed above, modalities other than CT and PET may be employed with the multi-modality imaging system 10.

The gantry 13 includes an x-ray source 15 that projects a beam of x-rays toward a detector array 18 on the opposite side of the gantry 13. Detector array 18 is formed by a plurality of detector rows (not shown) including a plurality of detector elements which together sense the projected x-rays that pass through a medical patient 22. Each detector element produces an electrical signal that represents the intensity of an impinging x-ray beam and hence allows estimation of the attenuation of the beam as it passes through the patient 22. During a scan to acquire x-ray projection data, gantry 13 and the components mounted thereon rotate about a center of rotation.

In certain embodiments, the multi-modality imaging system 10 may include a common controller or processor 25 configured to operate both the CT imaging system 11 and the PET imaging system 12. In other embodiments, the CT and the PET imaging systems may each include a dedicated controller that separately controls the CT and the PET imaging systems.

FIG. 2 is a block schematic diagram of the PET imaging system 12 illustrated in FIG. 1 in accordance with an embodiment of the present invention. The PET imaging system 12 includes a detector ring assembly 40 including a plurality of detector crystals. The PET imaging system 12 also includes a controller or processor 44, to control normalization and image reconstruction processes. Controller 44 is coupled to an operator workstation 46. In one non-limiting example, the controller 44 may be an example of the controller 25 of FIG. 1. Controller 44 includes a data acquisition processor 48 and an image reconstruction processor 50, which are interconnected via a communication link 52. PET imaging system 12 acquires scan data and transmits the data to data acquisition processor 48. The scanning operation is controlled from the operator workstation 46. The data acquired by the data acquisition processor 48 is reconstructed using the image reconstruction processor 50.

The detector ring assembly 40 includes a central opening, in which an object or patient, such as patient 22, may be positioned using, for example, a motorized table 24 (shown in FIG. 1). The motorized table 24 is aligned with the central axis of detector ring assembly 40. This motorized table 24 moves the patient 22 into the central opening of detector ring assembly 40 in response to one or more commands received from the operator workstation 46. A PET scanner controller 54, also referred to as the PET gantry controller, is provided (e.g., mounted) within PET system 12. The PET scanner controller 54 responds to the commands received from the operator workstation 46 through the communication link 52. Therefore, the scanning operation is controlled from the operator workstation 46 through PET scanner controller 54.

During operation, when a photon collides with a crystal 62 on a detector ring 60, it produces a scintillation on the crystal. Each photomultiplier tube produces an analog signal that is transmitted on communication line 64 when a scintillation event occurs. A set of acquisition circuits 66 is provided to receive these analog signals. Acquisition circuits 66 produce digital signals indicating the three-dimensional (3D) location and total energy of the event. The acquisition circuits 66 also produce an event detection pulse, which indicates the time or moment the scintillation event occurred. These digital signals are transmitted through a communication link, for example, a cable, to an event locator circuit 68 in the data acquisition processor 48.

The data acquisition processor 48 includes the event locator circuit 68, an acquisition CPU 70, and a coincidence detector 72. The data acquisition processor 48 periodically samples the signals produced by the acquisition circuits 66. The acquisition CPU 70 controls communications on a back-plane bus 74 and on the communication link 52. The event locator circuit 68 processes the information regarding each valid event and provides a set of digital numbers or values indicative of the detected event. For example, this information indicates when the event took place and the position of the scintillation crystal 62 that detected the event. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, the time markers in each event data packet must be within a predetermined time period, for example, 12.5 nanoseconds, of each other, to indicate coincidence. Second, the line-of-response (LOR) formed by a straight line joining the two detectors that detect the coincidence event should pass through the field of view in the PET imaging system 12. Events that cannot be paired are discarded. Coincident event pairs are located and recorded as a coincidence data packet that is communicated through a physical communication link 78 to a sorter/histogrammer 80 in the image reconstruction processor 50.

The image reconstruction processor 50 includes the sorter/histogrammer 80. During operation, sorter/histogrammer 80 generates a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory, which carry out the function of creating the histogram.

The image reconstruction processor 50 also includes a memory module 82, an image CPU 84, an array processor 86, and a communication bus 88. During operation, the sorter/histogrammer 80 counts all events occurring along each projection ray and organizes the events into 3D data. This 3D data, or sinogram, is organized in one exemplary embodiment as a data array 90. Data array 90 is stored in the memory module 82. The communication bus 88 is linked to the communication link 52 through the image CPU 84. The image CPU 84 controls communication through communication bus 88. The array processor 86 is also connected to the communication bus 88. The array processor 86 receives data array 90 as an input and reconstructs images in the form of image array 92. Resulting image arrays 92 are then stored in memory module 82.

The images stored in the image array 92 are communicated by the image CPU 84 to the operator workstation 46. The operator workstation 46 includes a CPU 94, a display 96, and an input device 98. The CPU 94 connects to communication link 52 and receives inputs, e.g., user commands, from the input device 98. The input device 98 may be, for example, a keyboard, mouse, a touch-screen panel, and/or a voice recognition system, and so on. Through input device 98 and associated control panel switches, the operator can control the operation of the PET imaging system 12 and the positioning of the patient 22 for a scan. Similarly, the operator can control the display of the resulting image on the display 96 and can perform image-enhancement functions using programs executed by the workstation CPU 94.

During PET imaging, radiotracers such as fluorine-18, carbon-11, nitrogen-13, oxygen-15, and the like are injected into a subject or patient. The radiotracers accumulate within organs, vessels or the like, and begin to decay and emit positrons. The positrons encounter electrons and, when occurs positron collides with an electron, the positron is annihilated and converted into two photons, or gamma rays. Each gamma ray has an energy of essentially 511 keV upon annihilation, and the two gamma rays are directed in substantially opposite directions.

The photons generated from the positron annihilation are absorbed and may be scattered in the attenuating medium (e.g., tissue, bones). Such scattered events may degrade the quality and accuracy of the reconstructed PET images. Various attenuation and scatter correction methods have been developed to compensate for these effects. An example method for estimating and correcting for scatter events occurring within a field-of-view of the PET scanner includes a single scatter simulation (SSS) model. In the SSS model, the number of scattered events for each sinogram bin or line-of-response (LOR) is estimated from an estimate of the PET radiotracer activity and applying an attenuation correction factor to the PET radiotracer activity inside a FOV of the PET scanner.

The SSS model uses emission and transmission images to estimate the scattered events along each line of response. Herein, the transmission image is acquired using the CT image and is further used for calculating attenuation coefficients as described later in the description.

The scatter distribution is calculated by summing the estimated scatter probabilities for each possible scatter point in the transmission image and each detector pair. In a simplified form, the SSS model used to estimate the scatter distribution may be a function of several variables, as shown below in equation (1):

$$R_{scat} = \int_{V_s} dV_s \frac{\sigma}{4\pi R^2} \frac{\mu}{\sigma_C} \frac{d\sigma_C}{d\Omega} \left( \varepsilon_1 l_1 \int_S^{A_1} \lambda ds + \varepsilon_2 l_2 \int_S^{A_2} \lambda ds \right) \quad (1)$$

where $R_{scat}$ represents the total coincidence rate in the LOR due to single scattered events and is represented as a volume integral over scatter volume $V_s$, $\sigma$ represents the geometrical cross section factor of the pair of detectors, R represents the distance from the scatter point to detector surfaces, $\mu$ represents linear attenuation coefficient, $\sigma_c$ represents the Compton interaction cross section, $d\sigma_c/d\Omega$ represents differential scattering cross section and is computed from the Klein-Nishina formula, $\epsilon$ represents the detector efficiency factors, l represents the summed attenuation factors along the photon path from the scatter point to the detectors, $A_1$ and $A_2$ represent the two detectors that detect the two scattered gamma photons, and $\lambda$ represents the emitter density.

The SSS model requires known emission activity and attenuation coefficients. Within the current FOV, an initial PET image reconstruction is performed to estimate the emission activity within the FOV. However, the emission activity outside the current scanner FOV may not be unknown since PET image reconstruction may have not been executed for activity outside the current FOV. Without knowing the emission activity outside the FOV, it is not possible to adapt the SSS model to estimate the OOF scatter. Not accounting for OOF scatter may lead to artifacts in the PET image, as shown in FIG. 3.

Turning to FIG. 3, it shows an example PET image 300 having a bladder region 308 residing inside a FOV 304 of a PET scanner, and muscle region 310 residing outside a FOV 304 of a PET scanner. The bladder can accumulate a large amount of radiotracer and as such there is increased emission activity originating from the bladder. In some examples, such regions may be referred as "hot spots". Uncorrected OOF scatter from the bladder 308 causes the shadow artifact 302 outside PET frame 304. Conversely, uncorrected OOF scatter from the muscle 310 generates the washout artifact 306 within the FOV 304.

The inventors have recognized that it may be possible to estimate OOF scatter and reduce image artifacts in the PET images that are caused by radiotracer uptake in organs lying outside the FOV of the scanner. Herein, the organs lying outside the FOV are identified using the CT image as described below.

Turning now to FIG. 4, an example method 400 for estimating OOF scatter using CT images is shown. Specifically, CT images acquired prior to a PET scan are segmented to define contours of the body and/or organs lying outside the FOV of the PET scanner.

Instructions for carrying out method 400 herein may be executed by a processor (e.g., processor or controller 25 of FIG. 1 and/or controller 44 of FIG. 2) based on instructions stored on a memory of the processor and in conjunction with signals received from sensors of the imaging system, such as the sensors described above with reference to FIGS. 1-2. The processor may employ actuators of the CT imaging system to adjust the operation of the imaging system, the collimators, and the detectors, according to the methods described below.

Method 400 begins at 405 wherein the controller receives radiotracer information from a user (e.g., operator) of an imaging system. In one non-limiting example, the imaging system may be a multi-modality system (such as the multi-modality system 10 shown in FIG. 1). In one example, the multi-modality system may include a CT imaging system and a PET imaging system as described with reference to FIGS. 1 and 2.

Receiving radiotracer information from the user includes a type of radiotracer that is injected into a patient positioned within the imaging system. The radiotracer may be a positron-emitting radionuclide. Some non-limiting examples of the radiotracers include fluorine-18 fludeoxyglucose (FDG), carbon-11 choline, nitrogen-13 ammonia, and oxygen-15 water. In some examples, the type of radiotracer injected may depend on the anatomy of interest that is being imaged.

The radiotracers injected into the patient may accumulate within organs, vessels or the like, and begin to decay and emit positrons. As explained previously, the positrons annihilate, generating a pair of gamma rays. The PET system detects the pair of gamma rays emitted by the radiotracer. In addition to the type of tracer injected, the controller may receive additional information such as a time of injection, a dose of radiotracer injected, and a pre-injection delay. In addition to radiotracer information, the controller may receive a weight of the subject. In one example, the operator of the imaging system may enter the weight of the patient.

At 410, method 400 includes performing a CT scout scan. The CT scout scan serves as an anatomical reference for the PET/CT scan. In one example, the CT scout scan may be used to define the starting and ending locations of the CT and PET acquisitions. In some examples, the CT scout scan may be a whole body scan. Once the starting and ending locations are defined, the method includes acquiring additional CT image data 415 within the region defined by the starting and the ending locations.

At 420, method 400 includes performing CT image segmentation on the CT image generated from the CT scan performed at 415. Image segmentation is the process of dividing an image into regions or segments with similar properties such as gray level, color, texture, brightness, and contrast. The process of segmentation subdivides objects or regions in an image to aid in the study of anatomical structures, identify a region-of-interest (ROI), and the like. Contours are generated around the segments to delineate anatomical structures within the image. As an example, contours may be generated to identify and locate organs such as liver, brain, bladder, lung, heart, muscle, and the like in the image. In this way, by segmenting the CT image, major organs such as bladder, liver, lung, brain, heart, and the like (also called anatomical landmarks) may be identified within the CT image of the patient as shown in FIG. 5.

Turning to FIG. 5, a pictorial view 500 shows organs segmented from a CT image 502. Specifically, the CT image 502 is generated by performing a CT scan as described with reference to 415 of method 400. Herein, the CT image 502 includes a full body CT image. Once the CT image 502 is generated, image segmentation may be performed on the generated CT image 502.

In one example, the image segmentation on the CT image 502 may be performed manually by a user of the imaging system. Herein, the user may identify organs in the CT image 502 and draw contours around the different organs using graphic interfaces, and manually delineate anatomical structures of the CT image. In another example, the controller may perform image segmentation of the CT image automatically (e.g., with no user intervention) and further automatically draw contours to identify the segmented anatomies. In some examples, the image segmentation may be semi-automated (e.g., part automated and part manual). As an example, in a semi-automated method, the user may provide some information (e.g., manually select a region to be segmented) while the identification of the region may be performed automatically (e.g., by comparing the selected region with organs in a look-up-table).

The CT image 502 may be segmented using various image segmentation techniques. Some non-limiting examples of image segmentation techniques include threshold or amplitude-based segmentation, edge-based segmentation, region-based segmentation, clustering techniques, and matching. As an example, in threshold-based segmentation, segmentation of an image is based on thresholding of histogram features and gray level thresholding. Mathematically the threshold can be defined by as shown in equation (2):

$$r_i = \begin{cases} 1, & P_i \geq T \\ 0, & P_i < T \end{cases} \qquad (2)$$

where $P_i$ is the pixel input of the image, $r_i$ is the segmentation mask for image pixel i, and T is the threshold.

The image is segmented or divided into two regions based on the threshold T. In one example, the threshold T may be set by the user. In another example, the controller may estimate T based on a histogram of the image. For example, the controller may generate the histogram of the CT image, and may select the threshold based on minima (e.g., lowest values of the histogram) occurring in the histogram. Herein, equation (2) is used to segment two regions within the CT image. To segment multiple regions within the CT image, different thresholds or threshold ranges may be used as shown in equation (3):

$$r_i = \begin{cases} 1, & T_1 < P_i \leq T_2 \\ 2, & T_2 < P_i \leq T_3 \\ 3, & T_3 < P_i \leq T_4 \\ k, & T_k < P_i \leq T_{k+1} \\ 0 & \text{otherwise} \end{cases} \quad (3)$$

where $T_1$ to $T_{k+1}$ are different thresholds set for different regions of the image. In this way, the image may be segmented into different regions using the threshold segmentation technique.

An edge-based segmentation technique includes segmenting the image based on detection of edges (e.g., boundaries which separate distinct regions). The edge detection method is based on marking of discontinuities in gray level and color, for example. This method divides an image on the basis of boundaries. Edges may be detected based on gradient function (e.g., using derivative operation), for example. Further, in edge based segmentation technique, borders or contours may be generated by combining the detected edges. Some examples of edge-based segmentation algorithm include edge relaxation, border detection method, and Hough transform method.

Region-based segmentation techniques are based on the principle of homogeneity-pixels with similar properties are clustered together to form a homogenous region. A starting or seeding point initializes the process of region based segmentation. In one example, the controller may select the seeding point. In another example, the user may select the seeding point. Once the seeding point is determined, regions are grown iteratively by merging neighboring or adjacent pixels based on a merging criteria. The process of merging may be continuous until all the pixels are assigned to respective regions. In this way, region-based segmentation may be used to delineate anatomical structures in the image.

In some example, various image segmentation techniques may be used in combination to segment or segregate the CT image to highlight anatomical structures such as muscles, bones and lungs. In some embodiments, information related to the anatomy, shape, size, and features of different organs is compiled in the form of atlas or look up table (LUT). The controller may use the LUT to identify and classify the anatomy in the CT image.

As described above, various methods may be used to segment the CT image 502, and additionally, contours representing the boundaries of the different structures may be drawn in the segmented CT image 504. For example, a contour 506 may be generated in the segmented CT image 504 based on one or more image segmentation methods described previously, to delineate an organ or anatomy in the CT image 504. Based on the size, shape, and location of the contour 506, the controller may be able to compare the contour 506 with images in the LUT and identify that the contour 506 represents the brain. Likewise, the controller may segment other organs in the CT image, draw contours around the organs, and identify the organs. For example, a contour 508 may represent the left lung, a contour 510 may represent the right lung, a contour 514 may represent the liver, and a contour 512 may represent the bladder. Herein, the controller performs image segmentation on the CT image to identify anatomical landmarks within the body of the patient. In this way, the controller may segment the CT image, and delineate anatomical structures within the CT image. By segmenting the CT images, the controller may be able to identify the anatomical landmarks and determine the position of these landmarks in the whole body, for example.

In some examples, the contours thus generated may be used to determine attenuation coefficients. Attenuation is the loss of detection of true coincidence events in PET systems, because of the absorption of the true coincidence events in the body. In PET imaging, photons that originate from structures deeper in the body are more highly attenuated than those originating closer to the surface. This effect of attenuation is typically accounted for in the PET image by using the CT scan data. Herein, the CT is a transmission scan that is used to generate an attenuation map that is used to correct this attenuation effect. For example, the attenuation of x-rays is given by equation (4):

$$I_{CT} = \int (I_0(E) e^{-\int_0^L \mu_l(E) dl}) dE \quad (4)$$

where $I_0(E)$ represents the initial x-ray intensity, and dl represents the incremental length of the material with attenuation coefficient $\mu_l(E)$. Herein, the CT contour may be generated after the CT scan using image segmentation techniques described previously. The CT attenuation coefficients $\mu_l(E)$ described in equation (4) may be calculated along the contour generated by the CT scan. Because of the lower photon energy of the CT x-rays (E=100-140 kVp), the CT attenuation coefficients are scaled to reflect the attenuation of the high-energy 511 keV emission photons first. Once scaled, the CT attenuation coefficients may be stored in memory, and retrieved during PET image reconstruction.

At 425, method 400 includes performing the PET scan and acquiring emission data or activity from inside the FOV. The PET scan may generate functional images corresponding to dynamic occurrences such as metabolism. Detector crystals of the PET imaging system detect gamma rays emitted from the patient, and acquisition circuits, event locator circuits, and a coincidence detector together record coincidence events which are the basis of the PET data. All positron emitting organs inside and outside the FOV may contribute to the detected gamma photons by the PET detectors. Herein, each organ inside and outside the FOV may be identified based on image segmentation performed on the CT image at 420.

At 428, the PET data may be reconstructed into a PET image. Reconstructing the PET image includes generating the PET image of organs inside a field-of-view of the PET scanner. As explained previously with reference to FIG. 2, an image reconstruction processor of the PET imaging system may include a sorter/histogrammer (such as sorter/histogrammer 80 of FIG. 2). The histogrammer includes a histogram which includes a large number of bins, where each bin corresponds to a unique pair of detector crystals in the PET scanner. Each bin of the histogram also stores a count value representing the number of coincidence events detected by the pair of detector crystals for that bin during the scan. At the end of the scan, the data in the histogram is used to reconstruct the PET image of the patient.

To perform quantitative PET image reconstruction 428, it may be desirable to accurately estimate the scattered events. If not accounted for or incorrectly estimated, scatter events may reduce the quality of PET images and introduce incorrect quantitation in PET imaging.

The single scatter simulation (SSS) model has been commonly used to estimate scattered events during PET image reconstruction. The SSS model requires knowledge of the emission activity and the attenuation coefficients. Within the current FOV, the emission activity can be estimated by an initial PET image reconstruction using the acquired PET data within the FOV.

Outside the current FOV, the emission activity can be estimated using the segmented CT images from 420 and the estimated organ emission activity from 430. At 430, method 400 includes estimating radiotracer uptake intensity in each segmented organ of the CT image. Herein, the organs are segmented using the CT image as described previously with reference to 420 of method 400. The radiotracer injected into the subject may be accumulated in organs. An increased uptake of the radiotracer in an organ may appear as a "hot spot" in the PET image. Abnormal tissue (or tumors) may have increased uptake and hence appear as hot spots in the PET image. However, normal tissues also uptake different levels of the radiotracer. For example, a radiotracer such as FDG is cleared primarily through the renal system, thus normal bladder might be the highest FDG uptake organ. The brain may have a higher FDG uptake than the adipose tissue, for example. Herein, the radiotracer uptake by normal tissues may be physiological whereas radiotracer uptake by abnormal tissues may be pathological. As explained previously, the CT image segmentation performed on the whole body at 420 may detect anatomical landmarks (such as bladder, liver, heart, brain, and the like) or hot spots.

The radiotracer uptake intensity in each organ may be based on several factors such as organ definition and intensity ratio of anatomical landmarks (such as liver, bladder, brain, and lung) to a background (e.g., muscle). Herein, the organ definition may include the contour of the segmented organ. For example, the radiotracer uptake in an organ may be proportional to a surface area of the contour. In addition, the radiotracer uptake intensity in each organ may be determined based on an intensity ratio of some major organ to the background (muscle). As discussed previously, some of the major organs such as liver, bladder, brain, lung, and the like may uptake increased amounts of the radiotracer, have increased intensity and appear as hot-spots in the PET image. The radiotracer uptake intensity in each organ may be determined based on the intensity ratio $I_r$ of some of the major organs (e.g., bladder and liver) with the background (e.g., muscle). Thus, the intensity ratio includes a ratio of PET activity in anatomical organs relative to PET activity in muscle. The radiotracer intensity ratio between major organs to the muscle may be pre-determined empirically. For example, it is typically assumed that the radiotracer intensity ratio between the liver and the muscle is 2:1 for $^{18}$F-FDG, and the radiotracer intensity in the lungs is zero. For different types of PET radiotracers, the typical radiotracer intensity ratio between major organs and the muscle may be read from a pre-determined look-up table.

At 435, method 400 includes estimating an emission activity from organs outside the FOV. For an organ outside the current FOV, the emission activity in that organ may be estimated by equation (5):

$$I_{organ} = I_r \times I_{muscle} \quad (5)$$

where $I_r$ is the radiotracer intensity ratio previously described, and $I_{muscle}$ is the radiotracer intensity in the muscle in the current PET imaging frame.

At 440, method 400 includes estimating a total scatter within FOV (or total FOV scatter). Several scatter correction techniques have been implemented to correct scatter in the PET images. Some example techniques include dual energy window, deconvolution, convolution subtraction, fitting analytical function, and model based techniques (e.g., Single Scatter Simulation (SSS) model described in equation (1)). The total scatter within the FOV may be estimated based on the attenuation coefficients $\mu$ and the PET emission activity $\lambda$. Mathematically, the total scatter within the FOV may be represented by equation (6):

$$S_{FOV} = F(\mu_{within\ FOV}, \lambda_{within\ FOV}) \quad (6)$$

where F is a function that applies the SSS model described by equation (1) to estimate scatter using $\mu$ and $\lambda$.

The axial coverage of a PET scanner can range from less than 10 cm to over 20 cm. Returning to FIG. 5, a region 516 in the CT image represents a FOV of a scanner. Herein, an area inside the FOV is smaller than an area outside the FOV. Thus, only a small section or region of the patient is covered by the scanner. Any scattered event that occurs outside the FOV of the scanner may contribute to inaccuracy in the PET image.

At 445, method 400 includes estimating a total OOF scatter. As previously described, without knowing the emission activity outside the FOV, such as the case of prospective PET scanning and image reconstruction, the SSS model is not able to correct for activity originating from outside the FOV. However, the inventors have recognized that it may be possible to estimate OOF scatter using the segmented CT images for organs outside the current FOV. Thus, even without generating PET images outside the FOV, OOF scatter may be calculated based on CT contours generated on the CT images at 415. The main advantage is that the method may be easily employed in prospective scanning and reconstruction without disrupting the current PET scan protocols or workflow. For example, the workflow is continuous, without any interruptions and not going back and forth. Thus, estimating the scatter from outside the FOV is implemented without any delays. Without knowing the emission activity outside the axial FOV of the PET scanner, the controller is able to estimate the emission activity outside the FOV based on the segmented CT images and the PET radiotracer intensity ratio.

The OOF scatter may be estimated based on the segmented CT images, which generates the attenuation coefficient $\mu_{OOF}$ for organs outside the current FOV, and the estimated PET emission activity $\lambda_{OOF}$ outside the FOV. Mathematically, the total OOF scatter may be represented by equation (7):

$$S_{OOF} = F(\mu_{OOF}, \lambda_{OOF}) \quad (7)$$

where F is the same function as in equation (6) that applies the SSS model described by equation (1).

At 450, method 400 includes estimating a total scatter, $S_{total}$, in the system as a sum of the total FOV scatter and the total OOF scatter estimated at 440 and 445 of method 400 respectively, as shown in equation (8):

$$S_{total} = S_{FOV} + S_{OOF} \quad (8)$$

where $S_{FOV}$ represents the total scatter within the FOV of the PET scanner and $S_{OOF}$ is the total OOF scatter. In some example, the OOF scatter may also be referred to as scatter outside FOV.

At 455, method 400 includes applying the estimated scattered events, $S_{total}$ to the PET data. Herein, the PET data is the emission activity occurring within the FOV that is measured by the scanner. However, the scatter correction may include scatter correction for both events occurring within the FOV and outside the FOV. In this way, the controller may correct the PET data for scatter events occurring both within and outside the FOV. PET image reconstruction 460 is then performed using the estimated scattered events.

At 465, method 400 includes displaying one or more of the PET image and the CT image. In one example, both the PET images and the CT images may be displayed side by side. In another example, the PET image may be overlaid or fused with the CT image.

In this way, OOF scatter may be estimated using segmented CT images for organs outside the current FOV, such that it can be employed in prospective scanning and reconstruction without disrupting the current PET scan protocols. Further, OOF scatter-related image artifacts may be reduced. Prior to performing a PET scan of a patient, a CT scan may be performed. The image data acquired during the CT scan may be analyzed to determine the type of various anatomical landmarks of the patient. The PET radiotracer intensity for each organ may be calculated based on the radiotracer intensity ratio between an organ to the muscle.

Once the radiotracer uptake intensity is estimated for each organ, scattered events for both within the FOV scatter and OOF scatter may be estimated. Both within the FOV scatter and OOF scatter may be estimated using the SSS model, as the PET radiotracer intensity and the attenuation coefficients is known. The estimated scattered events for both within the FOV scatter and OOF scatter may be summed and applied to the PET scan data in order to generate a scatter-corrected PET image.

A technical effect of the disclosure is that estimating OOF scatter is achieved without prior knowledge of emission activity outside the axial FOV. Another technical effect of the disclosure is that the estimation of OOF scatter does not interfere with the current PET scan protocols. Therefore, it has no impact to the PET scanning workflow and can be easily employed. The main advantage is that the method may be easily employed in prospective scanning and reconstruction without disrupting the current PET scan protocols or workflow. Furthermore, the workflow is continuous, thus the CT scan is acquired at the start of the scanning protocol, and there is no switching from CT to PET or vice versa which may otherwise cause additionally delays. Thus, estimating the scatter from outside the FOV is implemented without any delays.

An embodiment relates to a method for an imaging system, comprising performing, with a scanner, a scan of a subject to acquire emission data and calculating an amount of external scatter contamination in the emission data based on an estimated emission activity originating from anatomies outside a field-of-view (FOV) of the scanner. The anatomies are identified based on an image segmentation analysis performed on an image generated in the imaging system, and the image is generated prior to acquiring the emission data.

The method may further comprise estimating the emission activity based on a radiotracer uptake intensity of a radiotracer injected in the subject prior to acquiring the emission data. In examples, the uptake intensity may be determined based on a relative radiotracer intensity ratio between an organ and muscle. For example, the radiotracer intensity ratio of a given organ (e.g., the bladder) relative to muscle may be predetermined and retrieved from memory, and the radiotracer intensity of muscle may be determined by the acquired emission data. By knowing the ratio and the calculated intensity of the muscle, the intensity of the organ may be determined.

In an example, the image is a computed tomography (CT) image acquired using a CT imaging system, and the emission data is positron emission tomography (PET) data.

The image segmentation analysis may include one or more of a threshold-based segmentation, an edge-based segmentation, a region-based segmentation, a clustering technique, and a matching technique.

The method may further comprise including a correction for scattered events in PET image reconstruction based on the amount of external scatter contamination. The method may further comprise displaying a PET image generated from the PET image reconstruction, e.g., on a display device.

Another embodiment of a method of an imaging system comprises performing, with a first scanner, a first scan and generating a first image from image data collected during the first scan; generating a second, segmented image from the first image; acquiring, with a second scanner, a first emission activity from a field-of-view (FOV) of the second scanner; estimating a second emission activity from outside the FOV based on the second, segmented image; estimating a scatter correction based on each of the first emission activity and the second emission activity; and generating a third image based on the first emission activity and scatter correction.

In an example, performing the first scan comprises performing a computed tomography (CT) scan, and acquiring the first emission activity comprises acquiring the first emission activity via a positron emission tomography (PET) scan. In an example, the CT scan is performed prior to the PET scan. The second segmented image may include contours of organs lying outside the FOV of the second scanner, and the second scanner may include a PET scanner.

The method may further comprise estimating the second emission activity from the organs based on a shape and size of the contours. The method may further comprise estimating the second emission activity based on a ratio of intensity of PET emission in an anatomical landmark relative to PET emission in background.

An embodiment of a computed tomography/positron emission tomography (CT/PET) system comprises a CT imaging system configured to acquire a CT image of a patient positioned in the CT/PET system; a PET imaging system configured to acquire emission activity within a field-of-view (FOV) of a scanner of the PET imaging system; a processor; and a memory storing executable instructions that when executed cause the processor to segment the CT image and identify contours of one or more organs in the CT image lying outside the FOV; estimate an out-of-field (OOF) PET activity based on a radiotracer uptake estimated based on one or more of a size and shape of the identified contours; and generate a PET image based on the emission activity within the FOV of the scanner and corrected by the OOF PET activity.

The memory may store additional executable instructions that when executed cause the processor to estimate the radiotracer uptake based on an intensity ratio. The intensity ratio may include a ratio of PET activity in anatomical organs relative to PET activity in muscle. The memory may store additional executable instructions that when executed cause the processor to acquire the CT image and segment the CT image prior to acquiring the emission activity using the PET imaging system.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
performing, with a scanner, a scan of a subject to acquire emission data;
initiating reconstruction of the emission data using an image reconstruction processor;
executing instructions stored in a memory that cause a processor to calculate an amount of external scatter contamination in the emission data, wherein external scatter contamination is calculated based on an estimated emission activity originating from anatomies outside a field-of-view (FOV) of the scanner prior to the memory instructing the processor to calculate scatter originating within the FOV;
wherein the anatomies are identified based on an image segmentation analysis performed on an image generated in the imaging system;
executing instructions stored in the memory to calculate a total scatter by summing a total FOV scatter and a total OOF scatter;
applying the total scatter to the emission data to correct the emission data;
completing reconstruction of the emission data acquired by the processor using the image reconstruction processor, wherein the reconstructed emission data is corrected emission data; and
displaying reconstructed emission data;
wherein the image generated in the imaging system is acquired from the imaging system prior to acquiring the emission data.

2. The method of claim 1, further comprising estimating the emission activity based on a radiotracer uptake intensity of a radiotracer injected in the subject prior to acquiring the emission data.

3. The method of claim 2, further comprising estimating the emission activity based on a relative radiotracer intensity ratio between an organ and a muscle.

4. The method of claim 1, wherein the image is a computed tomography (CT) image acquired using a CT imaging system, and wherein the emission data is positron emission tomography (PET) data.

5. The method of claim 1, wherein the image segmentation analysis includes one or more of a threshold-based segmentation, an edge-based segmentation, a region-based segmentation, a clustering technique, and a matching technique.

6. The method of claim 1, further comprising including a correction for scattered events in PET image reconstruction based on the amount of external scatter contamination.

7. The method of claim 6, further comprising displaying a PET image generated from the PET image reconstruction.

8. A method of an imaging system, comprising:
performing, with a first scanner, a first scan of a patient positioned in the imaging system;
acquiring image data from the first scanner;
generating a first image from the image data collected during the first scan;
executing, with a processor, segmentation of the first image, wherein instructions for the processor are stored in a memory;
generating a second, segmented image from the first image;
identifying contours of one or more organs in the first image, wherein the organs are outside of a field of view (FOV) of a second scanner;
acquiring a first emission activity from the FOV of the second scanner;
executing instructions in the memory that instruct the processor to estimate a second emission activity from outside the FOV of the second scanner based on the second, segmented image;
estimating a scatter correction based on each of the first emission activity and the second emission activity; and
generating a third image based on the first emission activity and the scatter correction.

9. The method of claim 8, wherein performing the first scan comprises performing a computed tomography (CT) scan, and acquiring the first emission activity comprises acquiring the first emission activity via a positron emission tomography (PET) scan.

10. The method of claim 9, wherein the CT scan is performed prior to the PET scan.

11. The method of claim 8, wherein the second segmented image includes contours of organs lying outside the FOV of the second scanner, the second scanner comprising a PET scanner.

12. The method of claim 11, further comprising estimating the second emission activity from the organs based on a shape and size of the contours.

13. The method of claim 8, further comprising estimating the second emission activity based on a ratio of intensity of PET emission in an anatomical landmark relative to PET emission in background.

14. A computed tomography/positron emission tomography (CT/PET) system, comprising:
a CT imaging system configured to acquire a CT image of a patient positioned in the CT/PET system;
a PET imaging system configured to acquire emission activity within a field-of-view (FOV) of a scanner of the PET imaging system;
a processor; and
a memory storing executable instructions that when executed cause the processor to:
segment the CT image and identify contours of one or more organs in the CT image lying outside the FOV;
estimate an out-of-field (OOF) PET activity based on a radiotracer uptake estimated based on one or more of a size and shape of the identified contours; and
generate a PET image based on the emission activity within the FOV of the scanner and corrected by the OOF PET activity,
wherein the memory stores additional executable instructions that, when executed, cause the processor to estimate the radiotracer uptake based on an intensity ratio.

15. The system of claim 14, wherein the intensity ratio includes a ratio of PET activity in anatomical organs relative to PET activity in muscle.

16. The system of claim 14, wherein the memory stores additional executable instructions that, when executed, cause the processor to acquire the CT image and segment the CT image prior to acquiring the emission activity using the PET imaging system.

* * * * *